(12) United States Patent
Nishimoto

(10) Patent No.: US 10,161,338 B2
(45) Date of Patent: Dec. 25, 2018

(54) AIR-FUEL RATIO SENSOR CONTROL UNIT

(71) Applicant: DENSO CORPORATION, Kariya, Aichi-pref. (JP)

(72) Inventor: Satoshi Nishimoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/674,642

(22) Filed: Aug. 11, 2017

(65) Prior Publication Data

US 2018/0179976 A1 Jun. 28, 2018

(30) Foreign Application Priority Data

Dec. 27, 2016 (JP) ................. 2016-253506

(51) Int. Cl.
*F02D 41/14* (2006.01)
*G01N 27/20* (2006.01)

(52) U.S. Cl.
CPC ........ *F02D 41/1495* (2013.01); *G01N 27/20* (2013.01); *F02D 2250/14* (2013.01)

(58) Field of Classification Search
CPC .. F02D 41/1495; F02D 2250/14; G01N 27/20
USPC ..... 324/31.05, 23.2, 579, 600, 623, 86, 597, 324/598, 618, 630, 67.859; 73/31.05, 73/23.2, 579, 600, 623, 86, 597, 598, 73/618, 630, 67.859; 204/406, 410, 421, 204/424, 425, 427
See application file for complete search history.

(56) References Cited

U.S. PATENT DOCUMENTS

| | | | | |
|---|---|---|---|---|
| 6,295,862 B1 * | 10/2001 | Kurokawa | ........... | G01N 27/417 204/410 |
| 8,593,162 B2 * | 11/2013 | Nakamura | .......... | F02D 19/0628 324/663 |
| 2011/0199709 A1 | 8/2011 | Ieda | | |

* cited by examiner

*Primary Examiner* — Melissa Koval
*Assistant Examiner* — Trung Nguyen
(74) *Attorney, Agent, or Firm* — Posz Law Group, PLC

(57) ABSTRACT

An air-fuel ratio sensor control unit connected with an air-fuel ratio sensor including a common terminal, a first terminal and a second terminal includes a common connection terminal connected with the common terminal, a first connection terminal connected with the first terminal, a second connection terminal connected with the second terminal, a voltage control circuit controlling a voltage of the first connection terminal, a resistor connected with the common connection terminal, a voltage sensing circuit sensing a two-end voltage of the resistor, a current applying circuit applying a constant current to the second connection terminal, and a determining unit sensing a change quantity of the two-end voltage by using the voltage sensing circuit and determining whether a disconnection failure of the first connection terminal occurs based on a sensing result of the change quantity.

6 Claims, 4 Drawing Sheets

AIR-FUEL RATIO SENSOR CONTROL UNIT

CROSS REFERENCE TO RELATED APPLICATION

This application is based on Japanese Patent Application No. 2016-253506 filed on Dec. 27, 2016, the disclosure of which is incorporated herein by reference.

TECHNICAL FIELD

The present disclosure relates to an air-fuel ratio sensor control unit.

BACKGROUND

According to JP2011-164035A, an air-fuel ratio sensor control unit connected with an air-fuel ratio sensor including two cells. In the air-fuel ratio sensor control unit, a circuit applying a voltage used to sensing an abnormality that is a connection abnormality to a connection terminal of a subject is separately provided to sense the abnormality of an electrical connection between the air-fuel ratio sensor control unit and the air-fuel ratio sensor.

SUMMARY

According to JP2011-164035A, it is necessary to separately provide the circuit apply the voltage used to sensing the abnormality to the connection terminal of the subject to sense the connection abnormality.

It is an object of the present disclosure to provide an air-fuel ratio sensor control unit which is connected with an air-fuel ratio sensor including two cells and a disconnection failure of a connection terminal connected with a terminal of the air-fuel ratio sensor can be sensed.

According to an aspect of the present disclosure, the air-fuel ratio sensor control unit is connected with an air-fuel ratio sensor including a first cell, a second cell, a common terminal that is a terminal shared by the first cell and the second cell, a first terminal that is a terminal of the first cell opposite to the common terminal, and a second terminal that is a terminal of the second cell opposite to the common terminal.

The air-fuel ratio sensor control unit includes a common connection terminal connected with the common terminal, a first connection terminal connected with the first terminal, and a second connection terminal connected with the second terminal.

The air-fuel ratio sensor control unit further includes a voltage control circuit controlling a voltage of the first connection terminal such that a voltage of the common connection terminal becomes a predetermined voltage, a resistor including an end connected with the common connection terminal, the resistor through which a current flowing through the common connection terminal flows, and a voltage sensing circuit sensing a two-end voltage that is a voltage between two ends of the resistor.

The air-fuel ratio sensor control unit further includes a current applying circuit applying a constant current to the second connection terminal and a determining unit.

The determining unit senses a change quantity of the two-end voltage generated by the constant current applied by the current applying circuit to the second connection terminal by using the voltage sensing circuit, and the determining unit determines whether a disconnection failure of the first connection terminal occurs based on a sensing result of the change quantity. When the disconnection failure of the first connection terminal occurs, an electrical connection between the first connection terminal and the first terminal of the air-fuel ratio sensor is cut off.

When the disconnection failure of the first connection terminal does not occur, the voltage control circuit functions normally. Thus, in a normal state that the disconnection failure of the first connection terminal does not occur, when the current applying circuit applies the constant current to the second connection terminal, the constant current flows through a current path between the second connection terminal and the first connection terminal via the second cell and the first cell.

When the current applying circuit applies the constant current to the second connection terminal in a case where the disconnection failure of the first connection terminal occurs, the constant current flows through a current path between the second connection terminal and the common connection terminal without flowing through the first cell. Thus, the constant current flows through the resistor, and a two-end voltage of the resistor changes. The determining unit can determine whether the disconnection failure of the first connection terminal occurs based on the change quantity of the two-end voltage.

Thus, the air-fuel ratio sensor control unit can sense the disconnection failure of the first connection terminal connected with the first terminal of the air-fuel ratio sensor without providing a circuit applying a voltage used to sense an abnormality to the first connection terminal.

BRIEF DESCRIPTION OF THE DRAWINGS

The above and other objects, features and advantages of the present disclosure will become more apparent from the following detailed description made with reference to the accompanying drawings. In the drawings.

DESCRIPTION OF EMBODIMENTS

Hereafter, referring to drawings, an embodiment of the present disclosure will be described.

Figure 1:
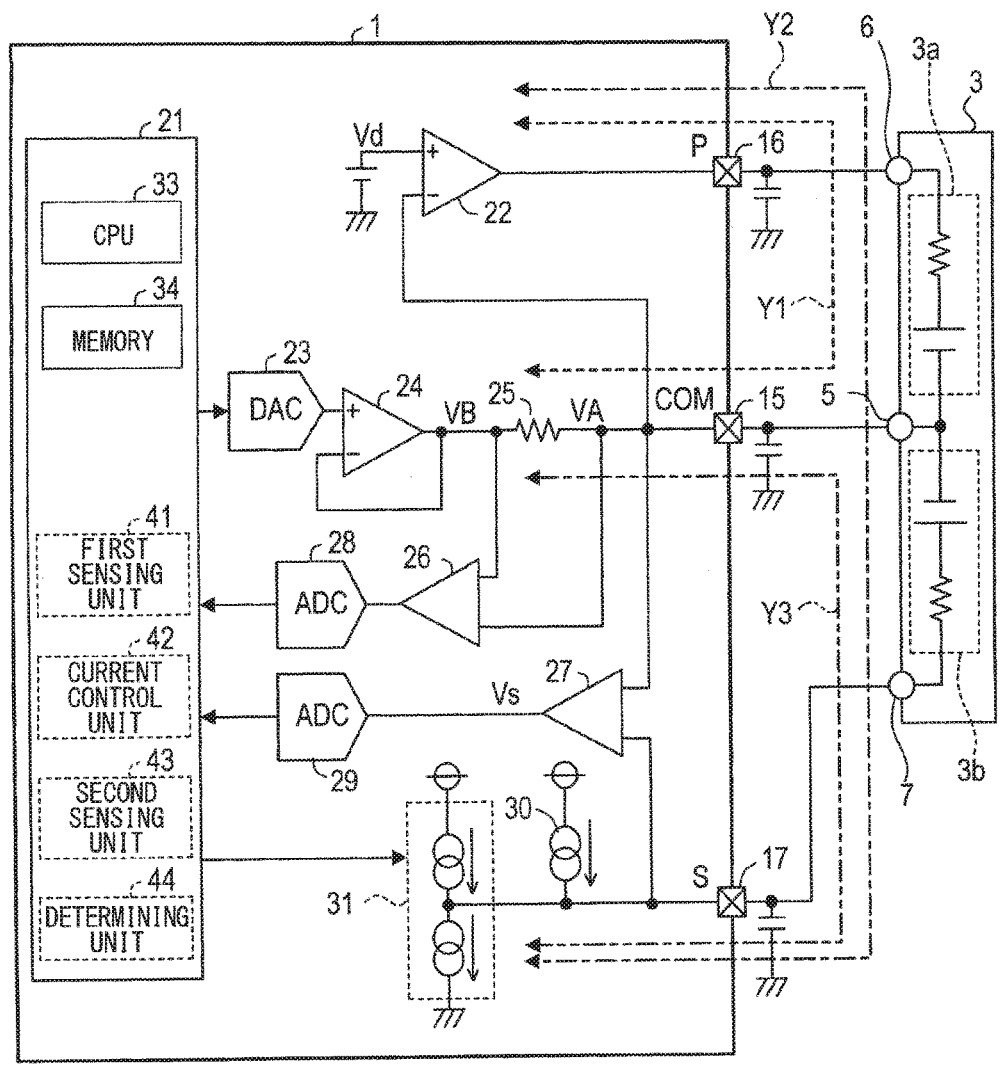
FIG. 1 is a schematic diagram showing an air-fuel ratio sensor control unit according to an embodiment of the present disclosure.

As show in FIG. 1, an air-fuel ratio sensor control unit 1 that is an ECU 1 is connected with an air-fuel ratio sensor 3 sensing an air-fuel ratio. According to the present embodiment, the ECU is short for an electronic control unit. According to the present embodiment, the air-fuel ratio sensor 3 is referred to as a sensor 3.

The sensor 3 is an air-fuel ratio sensor of a two-cell type includes two cells that are an oxygen pump cell 3a and an electromotive force cell 3b. According to the present embodiment, the oxygen pump cell 3a is referred to as a pump cell 3a. The sensor 3 is arranged in an exhaust passage of an engine of a vehicle. The sensor 3 is a sensor that a current flowing through the pump cell 3a is a sensor current indicating the air-fuel ratio. In the sensor 3, the pump cell 3a is driven such that an electromotive force of the electromotive force cell 3b obtained in response to a difference in oxygen concentrations between a diffusion chamber to which an exhaust gas is introduced and a reference oxygen chamber becomes a target voltage value. In this case, the electromotive force of the electromotive force cell 3b is equivalent to an output voltage of the electromotive force cell 3b. Further, the sensor current is equivalent to an output of the sensor 3.

The sensor 3 includes three terminals 5, 6 and 7 that are a common negative terminal 5 that is a negative terminal of the pump cell 3a and is also a negative terminal of the electromotive force cell 3b, a first positive terminal 6 that is a positive terminal of the pump cell 3a, and a second positive terminal 7 that is a positive terminal of the electromotive force cell 3b. The common negative terminal 5 is shared by the pump cell 3a and the electromotive force cell 3b. The pump cell 3a is equivalent to a first cell, and the electromotive force cell 3b is equivalent to a second cell. The common negative terminal 5 is equivalent to a common terminal, the first positive terminal 6 is equivalent to a first terminal, and the second positive terminal 7 is equivalent to a second terminal.

The ECU 1 includes a common connection terminal 15 connected with the common negative terminal 5 of the sensor 3, a first connection terminal 16 connected with the first positive terminal 6 of the sensor 3, and a second connection terminal 17 connected with the second positive terminal 7 of the sensor 3. The common connection terminal 15 is equivalent to a COM-terminal 15, the first connection terminal 16 is equivalent to a P-terminal 16, and the second connection terminal 17 is equivalent to an S-terminal 17.

The ECU 1 further includes a microcomputer 21 that is a control unit, a voltage control circuit 22, a D-A converter 23, a buffer circuit 24, a resistor 25 that is used to sense a current, amplifier circuits 26 and 27 that are a first amplifier circuit 26 and a second amplifier circuit 27, A-D converters 28 and 29 that are a first A-D converter 28 and a second A-D converter 29, a constant current circuit 30, and a current applying circuit 31.

The microcomputer 21 includes a CPU 33 and a semiconductor memory 34 including a RAM, a ROM, and a flash memory. According to the present embodiment, the semiconductor memory 34 is referred to as a memory 34. When the CPU 33 executes programs stored in a non-transitional substantial storage media, the microcomputer 21 achieves various functions. According to the present embodiment, the memory 34 is the non-transitional substantial storage media in which the programs are stored. Further, when the programs are executed, methods corresponding to the programs are executed. A total number of microcomputer(s) constituting the ECU 1 is not limited to one, and the total number may be more than one.

The microcomputer 21 further includes a first sensing unit 41, a current control unit 42, a second sensing unit 43, and a determining unit 44 which are correlative to functions achieved by the CPU 33 executing the programs.

The first sensing unit 41 executes a first sensing operation to sense the sensor current indicating the air-fuel ratio. The current control unit 42 executes a current control operation to control the current applying circuit 31. The second sensing unit 43 executes a second sensing operation to sense an impedance of the electromotive force cell 3b. The determining unit 44 executes a determining operation to determine whether a disconnection failure of the P-terminal 16 occurs. When the disconnection failure of the P-terminal 16 occurs, an electrical connection between the P-terminal 16 and the first positive terminal 6 of the sensor 3 is cut off.

According to the present embodiment, functions of the units 41 to 44 are not limited to be achieved by using software, at least a part of the functions of the units 41 to 44 may be achieved by using one or more hardware. For example, when the functions are achieved by using hardware such as electronic circuits, the electronic circuits may include a digital circuit including plural logic circuits, or an analog circuit, or a combination of the digital circuit(s) and the analog circuit(s).

The constant current circuit 30 applies a constant current that is used to generate the electromotive force at the electromotive force cell 3b to the S-terminal 17. The constant current applied to the S-terminal 17 is applied to the second positive terminal 7 of the sensor 3.

The second amplifier circuit 27 amplifies an S-COM voltage that is a voltage between the S-terminal 17 and the COM-terminal 15 and then outputs the S-COM voltage. The S-COM voltage is a voltage between two ends of the electromotive force cell 3b and is also the output voltage Vs of the electromotive force cell 3b. According to the present embodiment, an amplifying factor of the second amplifier circuit 27 is one. In other words, the second amplifier circuit 27 outputs an output voltage that is equal to the output voltage Vs of the electromotive force cell 3b. The second A-D converter 29 converts the output voltage of the second amplifier circuit 27 to a digital signal and then outputs the digital signal that is an A-D conversion result of the output voltage of the second amplifier circuit 27 to the microcomputer 21.

The voltage control circuit 22 is a circuit driving the pump cell 3a to sense the air-fuel ratio and is constituted by an operational amplifier that an output terminal of the operational amplifier is connected with the P-terminal 16. The voltage control circuit 22 controls a voltage of the P-terminal 16 such that a voltage of the COM-terminal 15 becomes a predetermined voltage Vd that is constant. According to the present embodiment, the predetermined voltage Vd is 2.5V. Further, the voltage of the COM-terminal 15 is referred to as a COM-terminal voltage, the voltage of the P-terminal 16 is referred to as a P-terminal voltage, and a voltage of the S-terminal 17 is referred to as an S-terminal voltage.

The D-A converter 23 outputs an output voltage when receiving a digital signal from the microcomputer 21. The buffer circuit 24 outputs an output voltage that is equal to the output voltage of the D-A converter 23.

The resistor 25 includes a first end connected with the COM-terminal 15. A current flowing through the resistor 25 is equal to a current flowing through the COM-terminal 15. The resistor 25 further includes a second end connected with an output terminal of the buffer circuit 24. In other words, the resistor 25 is arranged between the COM-terminal 15 and the buffer circuit 24.

The first amplifier circuit 26 amplifies a two-end voltage that is a difference in voltage between two ends of the resistor 25 and then outputs an output voltage that is the two-end voltage. According to the present embodiment, the two-end voltage of the resistor 25 is referred to as a resistor two-end voltage. The first A-D converter 28 converts the output voltage of the first amplifier circuit 26 to a digital signal and then outputs the digital signal that is an A-D conversion result of the output voltage of the first amplifier circuit 26 to the microcomputer 21.

The first sensing unit 41 senses the output voltage Vs of the electromotive force cell 3b based on the digital signal transmitted from the second A-D converter 29. The first sensing unit 41 controls the output voltage of the D-A converter 23 such that the output voltage Vs becomes the target voltage value. According to the present embodiment, the target voltage value is 0.45V. Thus, the sensor current that is a current corresponding to the air-fuel ratio flows through the pump cell 3a via the resistor 25. As shown in FIG. 1, a dashed line Y1 indicates a current path through which the sensor current corresponding to the air-fuel ratio flows. The first sensing unit 41 senses the sensor current based on the digital signal transmitted from the first A-D converter 28. Specifically, the first sensing unit 41 executes a conversion operation to convert a value of the digital signal acquired by the first A-D converter 28 to a current value that indicates the sensor current. The sensor current sensed by the first sensing unit 41 is used in an air-fuel ratio feedback control that corrects a fuel injection quantity such that the air-fuel ratio becomes a target ratio value.

Figure 2:
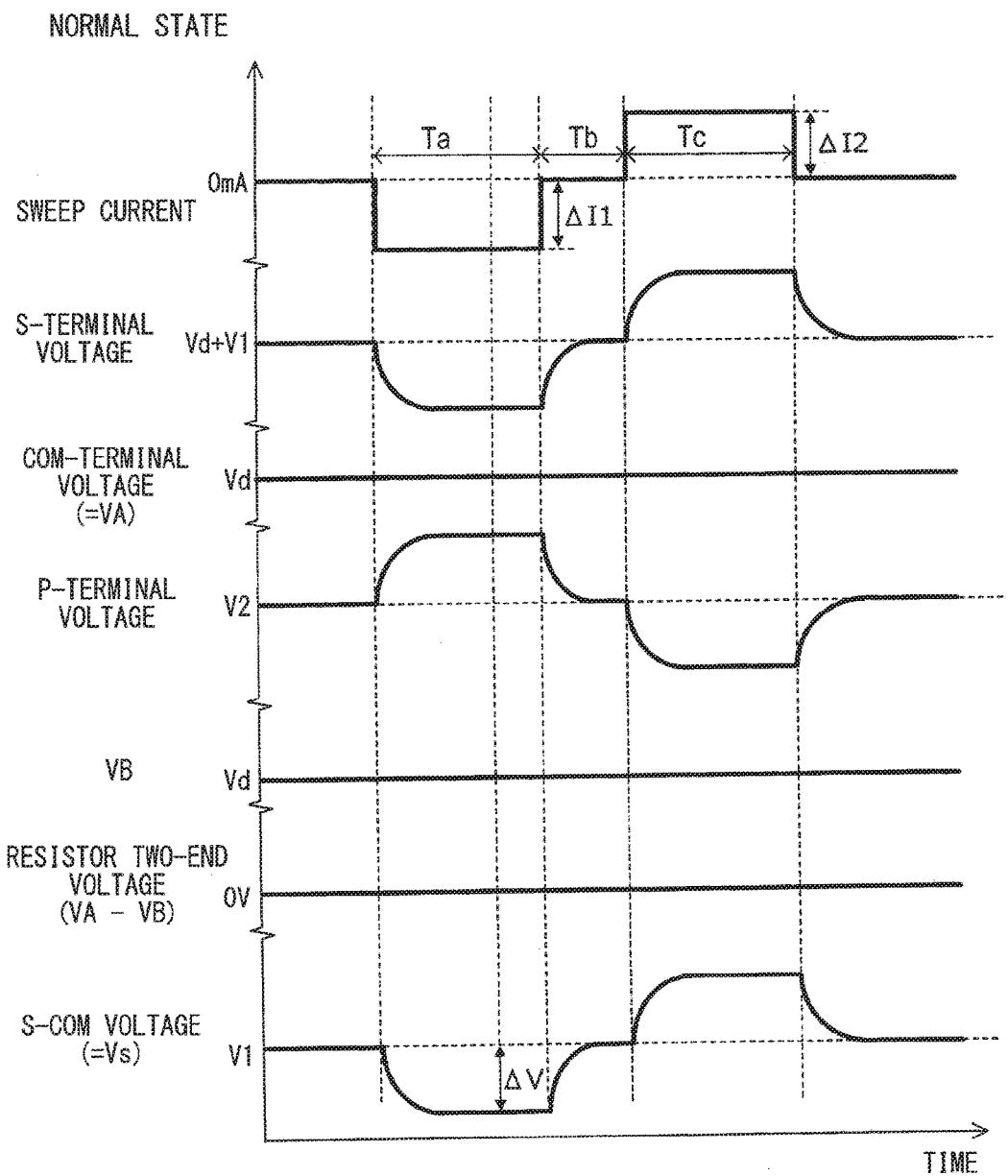
FIG. 2 is a time chart showing a sweep current applied by a current applying circuit and voltages in a normal state.

As show in FIG. 2, the current applying circuit 31 can apply constant currents $\Delta I1$ and $\Delta I2$ which flow in opposite directions to the S-terminal 17, respectively. According to the present embodiment, magnitudes of the constant currents $\Delta I1$ and $\Delta I2$ are equal to each other. However, according to the present disclosure, the magnitudes may be different. As shown in FIG. 2, a sweep current indicates the constant currents applied by the current applying circuit 31 to the S-terminal 17. The sweep current is a current changing to a positive value and a negative value with time. According to the present embodiment, as shown in FIG. 2, a direction of the constant current $\Delta I2$ that is a direction of a current flowing from the S-terminal 17 to the electromotive force cell 3b is a positive direction. In this case, the constant current $\Delta I2$ is a positive constant current $\Delta I2$. Then, the constant current $\Delta I1$ is a negative constant current $\Delta I1$.

The current control unit 42 controls to activate the current applying circuit 31 to sequentially apply the negative constant current $\Delta I1$ flowing in a negative direction and the positive constant current $\Delta I2$ flowing in the positive direction to the S-terminal 17. An applying operation that the negative constant current $\Delta I1$ and the positive constant current $\Delta I2$ are applied to the S-terminal 17 is executed every time that a specified time interval has elapsed. According to the present embodiment, the negative constant current $\Delta I1$ is equivalent to a first constant current, and the positive constant current $\Delta I2$ is equivalent to a second constant current. According to the present disclosure, an applying order of the negative constant current $\Delta I1$ and the positive constant current $\Delta I2$ may be reversed. In other words, the positive constant current $\Delta I2$ flowing in the positive direction may be applied to the S-terminal 17 in advance of the negative constant current $\Delta I1$ flowing in the negative direction. In this case, the positive constant current $\Delta I2$ is equivalent to the first constant current, and the negative constant current $\Delta I1$ is equivalent to the second constant current.

FIG. 2 is a time chart showing the S-terminal voltage, the COM-terminal voltage, the P-terminal voltage, a voltage VB of the second end of the resistor 25, the resistor two-end voltage and the S-COM voltage in a case where the constant currents $\Delta I1$ and $\Delta I2$ are sequentially applied to the S-terminal 17 in a normal state.

In the normal state, the disconnection failure of the P-terminal 16 does not occur. As shown in FIGS. 1 and 2, VA indicates the COM-terminal voltage. Thus, VA-VB indicates the resistor two-end voltage as shown in FIG. 2. According to the present embodiment, as shown in FIG. 2, V1 is an exemplary value of the output voltage Vs of the electromotive force cell 3b, and V2 is an exemplary value of the P-terminal voltage. In this case, V1 may be 0.45V.

The second sensing unit 43 loads the digital signal transmitted from the second A-D converter 29 before the current applying circuit 31 applies the negative constant $\Delta I1$ to the P-terminal 16, and loads the digital signal transmitted from the second A-D converter 29 in a time interval where the current applying circuit 31 applies the negative constant $\Delta I1$ to the P-terminal 16. The second sensing unit 43 senses a variation quantity $\Delta V$ of the voltage between two ends of the electromotive force cell 3b generated by the negative constant current $\Delta I1$ applied to the P-terminal 16 as shown in FIG. 2, based on the digital signal that is loaded. The second sensing unit 43 calculates the impedance of the electromotive force cell 3b based on the variation quantity $\Delta V$ that is sensed and a value of the negative constant current $\Delta I1$.

In the normal state, since the voltage control circuit 22 operates normally, the constant currents $\Delta I1$ and $\Delta I2$ applied by the current applying circuit 31 to the S-terminal 17 flow through a current path between the S-terminal 17 and the P-terminal 16 via two cells 3a and 3b as a dotted dashed line (center line) Y2 shown in FIG. 1. Thus, the constant currents $\Delta I1$ and $\Delta I2$ do not flow through the resistor 25. In other words, when the constant currents $\Delta I1$ and $\Delta I2$ are applied to the S-terminal 17, the resistor two-end voltage does not change as shown in FIG. 2. Further, as shown in FIG. 2, since a condition that the sensor current flowing through the resistor 25 corresponding to the air-fuel ratio is zero is indicated, the resistor two-end voltage maintains to be 0V.

Figure 3:
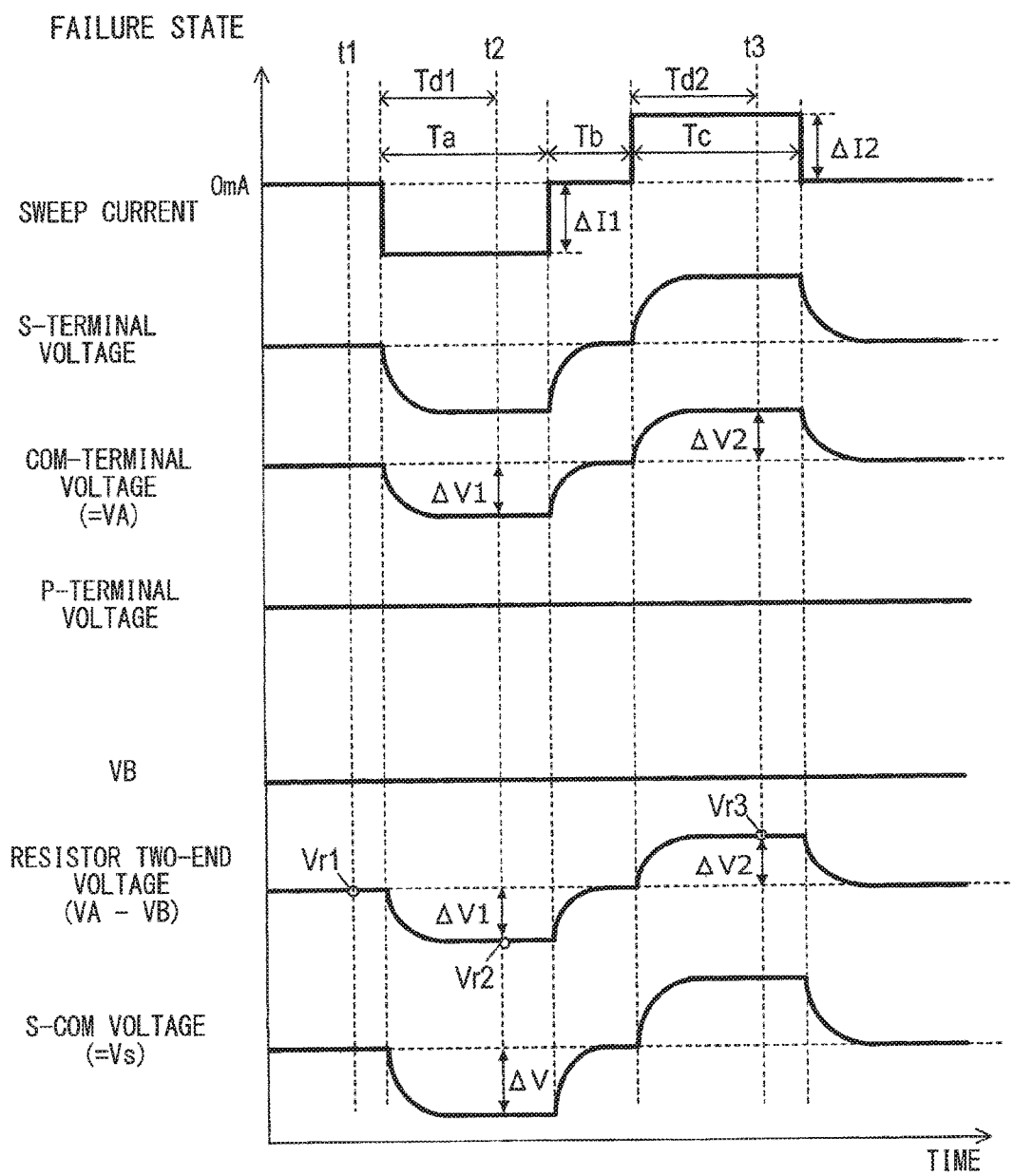
FIG. 3 is a time chart showing the sweep current and the voltages in a failure state where a disconnection failure of a P-terminal occurs.

When the current applying circuit 31 applies the constant currents $\Delta I1$ and $\Delta I2$ to the S-terminal 17 in a case where the disconnection failure of the P-terminal 16 occurs, the constant currents $\Delta I1$ and $\Delta I2$ flow through a current path between the S-terminal 17 and the COM-terminal 15 as a double-dotted dashed line (phantom line) Y3 shown in FIG. 1 without flowing through the pump cell 3a. Thus, the constant currents $\Delta I1$ and $\Delta I2$ flow through the resistor 25. In other words, when the constant currents $\Delta I1$ and $\Delta I2$ are applied to the S-terminal 17, the resistor two-end voltage changes as shown in FIG. 3. Further, as shown in FIG. 3, when the disconnection failure of the P-terminal 16 occurs, start values of the voltages that are values of the voltages before the constant current $\Delta I1$ and $\Delta I2$ are applied become unstable. Thus, the start values are not indicated in FIG. 3.

As the above description, the current paths through which the constant currents $\Delta I1$ and $\Delta I2$ applied to the S-terminal 17 flow are different in the normal state and in a failure state where the disconnection failure of the P-terminal 16 occurs. Thus, the determining unit 44 senses a change quantity of the resistor two-end voltage generated by the constant currents $\Delta I1$ and $\Delta I2$ applied to the S-terminal 17, and determines whether the disconnection failure of the P-terminal 16 occurs based on a sensing result of the change quantity.

Figure 4:
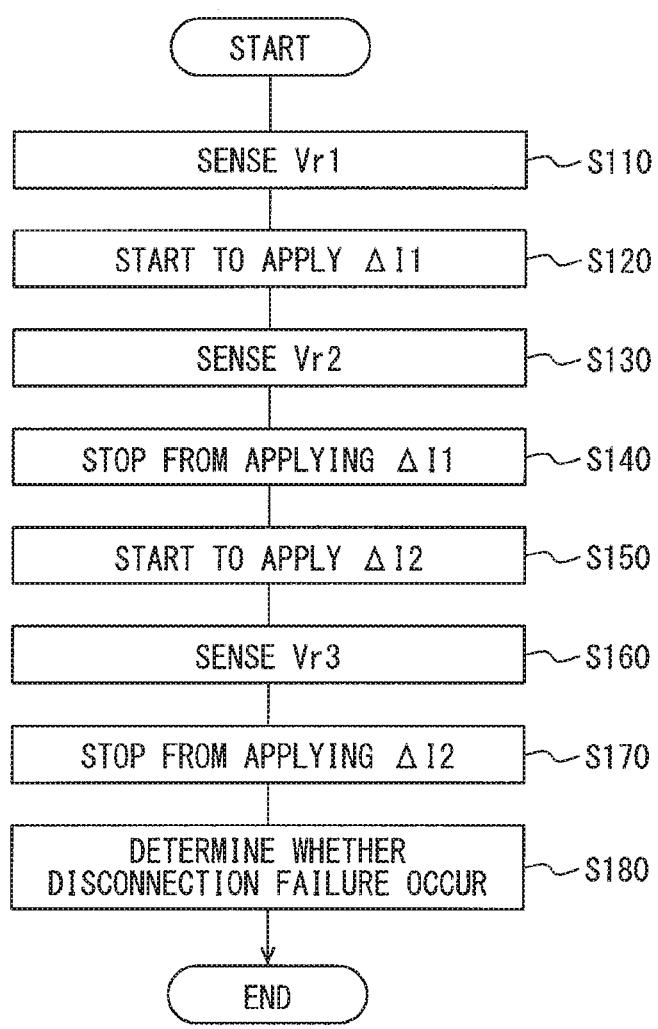
FIG. 4 is a flowchart showing a determining operation executed by a determining unit and a current control operation executed a current control unit.

Referring to FIG. 4, a determining operation executed by the determining unit 44 and a current control operation executed by the current control unit 42 will be described. The operations shown in FIG. 4 are executed at a specified time interval that is equivalent to a frequency of applying the constant currents $\Delta I1$ and $\Delta I2$ to the S-terminal 17. In the operations shown in FIG. 4, S110, S130, S160 and S180 are equivalent to the determining operation executed by the determining unit 44, and S120, S140, S150 and S170 are equivalent to the current control operation executed by the current control unit 42.

As shown in FIG. 4, when a present time is a timing that the constant currents $\Delta I1$ and $\Delta I2$ are controlled to be applied to the S-terminal 17, at S110, the determining unit 44 senses the resistor two-end voltage based on the digital signal transmitted from the first A-D converter 28 and then stores a sensing result of the resistor two-end voltage as Vr1.

At S120, the current control unit 42 controls the current applying circuit 31 to start to apply the negative constant current ΔI1 to the S-terminal 17.

When a first waiting time interval Td1 that is predetermined has elapsed since a timing that the current applying circuit 31 starts to apply the negative constant current ΔI1 to the S-terminal 17, at S130, the determining unit 44 senses the resistor two-end voltage based on the digital signal transmitted from the first A-D converter 28 again and then stores the sensing result of the resistor two-end voltage as Vr2.

When a first applying time interval Ta longer than the first waiting time interval Td1 has elapsed since the timing that the current applying circuit 31 starts to apply the negative constant current ΔI1 to the S-terminal 17, at S140, the current control unit 42 controls the current applying circuit 31 to stop from applying the negative constant current ΔI1 to the S-terminal 17.

When a switching time interval Tb has elapsed since a timing that the current applying circuit 31 stops from applying the negative constant current ΔI1 to the S-terminal 17, at S150, the current control unit 42 controls the current applying circuit 31 to start to apply the positive constant current ΔI2 to the S-terminal 17.

When a second waiting time interval Td2 has elapsed since a timing that the current applying circuit 31 starts to apply the positive constant current ΔI2 to the S-terminal 17, at S160, the determining unit 44 senses the resistor two-end voltage based on the digital signal transmitted from the first A-D converter 28 and then stores the sensing result of the resistor two-end voltage as Vr3. According to the present embodiment, the second waiting time interval Td2 is equal to the first waiting time interval Td1. However, the first waiting time interval Td1 and the second waiting time interval Td2 may be different.

When a second applying time interval Tc longer than the second waiting time interval Td2 has elapsed since the timing that the current applying circuit 31 starts to apply the positive constant current ΔI2 to the S-terminal 17, at S170, the current control unit 42 controls the current applying circuit 31 to stop from applying the positive constant current ΔI2 to the S-terminal 17. According to the present embodiment, the second applying time interval Tc is equal to the first applying time interval Ta. However, the first applying time interval Ta and the second applying time interval Tc may be different.

As shown in FIG. 3, the current control unit 42 controls the current applying circuit 31 to continuously apply the negative constant current ΔI1 to the S-terminal 17 in the first applying time interval Ta, and then controls the current applying circuit 31 to continuously apply the positive constant current ΔI2 to the S-terminal 17 in the second applying time interval Tc when the switching time interval Tb has elapsed.

At a timing t1 shown in FIG. 3, the determining unit 44 senses the resistor two-end voltage right before the current applying circuit 31 starts to apply the negative constant current ΔI1 to the S-terminal 17 and then stores the sensing result of the resistor two-end voltage as Vr1.

At a timing t2 shown in FIG. 3, the determining unit 44 senses the resistor two-end voltage when the first waiting time interval Td1 has elapsed since the timing that the current applying circuit 31 starts to apply the negative constant current ΔI1 to the S-terminal 17 and then stores the sensing result of the resistor two-end voltage as Vr2. In other words, the determining unit 44 senses the resistor two-end voltage in a time interval that the current applying circuit 31 continuously applies the negative constant current ΔI1 to the S-terminal 17 and then stores the sensing result of the resistor two-end voltage as Vr2.

At a timing t3 shown in FIG. 3, the determining unit 44 senses the resistor two-end voltage when the second waiting time interval Td2 has elapsed since the timing that the current applying circuit 31 starts to apply the positive constant current ΔI2 to the S-terminal 17 and then stores the sensing result of the resistor two-end voltage as Vr3. In other words, the determining unit 44 senses the resistor two-end voltage in a time interval that the current applying circuit 31 continuously applies the positive constant current ΔI2 to the S-terminal 17 and then stores the sensing result of the resistor two-end voltage as Vr3.

When the current applying circuit 31 stops from applying the positive constant current ΔI2 to the S-terminal 17 at S170, at S180, the determining unit 44 determines whether the disconnection failure of the P-terminal 16 occurs by using Vr1, Vr2 and Vr3 stored at S110, S130 and S160.

Specifically, the determining unit 44 calculates a deviation between Vr1 and Vr2 as ΔV1 and calculates a deviation between Vr1 and Vr3 as ΔV2 as shown in FIG. 3. In this case, the deviation is an absolute value of a difference between Vr1 and Vr2 or an absolute value of a difference between Vr1 and Vr3. According to the present embodiment, the determining unit 44 calculates a value obtained by subtracting Vr2 from Vr1 as ΔV1, and calculates a value by subtracting Vr1 from Vr3 as ΔV2. In other words, ΔV1=Vr1−Vr2, and ΔV2=Vr3−Vr1.

ΔV1 is the change quantity of the resistor two-end voltage generated by the negative constant current ΔI1 applied to the S-terminal 17. Thus, a theoretical value of ΔV1 of when the negative constant current ΔI1 flows through the resistor 25 is a value obtained by multiplying a resistance of the resistor 25 by the value of the negative constant current ΔI1. ΔV2 is the change quantity of the resistor two-end voltage generated by the positive constant current ΔI2 applied to the S-terminal 17. Thus, a theoretical value of ΔV2 of when the positive constant current ΔI2 flows through the resistor 25 is a value obtained by multiplying the resistance of the resistor 25 by a value of the positive constant current ΔI2.

The determining unit 44 calculates a total value that is a sum of ΔV1 and ΔV2. In other words, the total value=ΔV1+ΔV2. The determining unit 44 determines whether the total value is greater than or equal to a total threshold that is predetermined. When the determining unit 44 determines that the total value is greater than or equal to the total threshold, the determining unit 44 determines that the disconnection failure of the P-terminal 16 occurs. The total value (ΔV1+ΔV2) is a total change quantity of the resistor two-end voltage generated by the constant currents ΔI1 and ΔI2 applied to the S-terminal 17.

When the determining unit 44 determines that the total value is less than the total threshold, the determining unit 44 determines the disconnection failure of the P-terminal 16 does not occur. In this case, the P-terminal 16 is in the normal state. As shown in FIG. 2, in the normal state, when the constant currents ΔI1 and ΔI2 are applied to the S-terminal 17, the resistor two-end voltage does not change.

According to the ECU 1, following effects can be achieved.

The determining unit 44 senses the change quantities ΔV1 and ΔV2 of the resistor two-end voltage generated by the constant currents ΔI1 and ΔI2 applied by the current applying circuit 31 to the S-terminal 17, by using the first amplifier circuit 26 and the first A-D converter 28. The determining unit 44 determines whether the disconnection failure of the P-terminal 16 occurs based on a sensing result of the change quantities ΔV1 and ΔV2. Thus, the determining unit 44 can sense the disconnection failure of the P-terminal 16 without using a circuit applying a voltage used to sense an abnormality to the P-terminal 16. The first amplifier circuit 26 and the first A-D converter 28 are equivalent to a voltage sensing circuit sensing the resistor two-end voltage.

The resistor 25 used to sense the current is equivalent to a resistor that is used to sense a current flowing through the pump cell 31a as an output of the sensor 3. In other words, the resistor 25 used to sense the sensor current corresponding to the air-fuel ratio is also used to sense the disconnection failure of the P-terminal 16. Thus, an increasing of circuits constituting the ECU 1 can be suppressed.

The first amplifier circuit 26 and the first A-D converter 28 are equivalent to a circuit that is used to sense the current flowing through the pump cell 3a as the output of the sensor 3. In other words, the first amplifier circuit 26 and the first A-D converter 28 that are used to sense the sensor current are also used to sense the disconnection failure of the P-terminal 16. Thus, the increasing of circuits constituting the ECU 1 can be suppressed.

The current applying circuit 31 is equivalent to a circuit that is used to apply the constant currents ΔI1 and ΔI2 to the S-terminal 17 to sense the impedance of the electromotive force cell 3b. In other words, the current applying circuit 31 used to sense the impedance of the electromotive force cell 3b is also used to sense the disconnection failure of the P-terminal 16. Thus, the increasing of circuits constituting the ECU 1 can be suppressed.

The determining unit 44 senses the change quantity of the resistor two-end voltage by using the resistor two-end voltage Vr2 of when the negative constant current ΔI1 is applied to the S-terminal 17, and the resistor two-end voltage Vr3 of when the positive constant current ΔI2 is applied to the S-terminal 17. Thus, the change quantity of the resistor two-end voltage which is sensed when the disconnection failure of the P-terminal 16 occurs can be enlarged, and a determining accuracy of the disconnection failure can be improved.

According to the present disclosure, the determining unit 44 may calculate a deviation between Vr2 and Vr3 as the change quantity of the resistor two-end voltage. In this case, the deviation is obtained by subtracting Vr2 from Vr3, that is, the deviation=Vr3−Vr2. Further, since the deviation is equal to a sum of ΔV1 and ΔV2, the determining unit 44 can calculate ΔV1+ΔV2 as the change quantity of the resistor two-end voltage. Then, the determining unit 44 may not execute S110 shown in FIG. 4. In other words, S110 can be cancelled.

The present disclosure is not limited to the embodiments mentioned above, and can be applied to various embodiments within the spirit and scope of the present disclosure.

According to the present disclosure, the constant current applied to the S-terminal 17 to sense the disconnection failure of the P-terminal 16 may be one of the negative constant current and the positive constant current.

When the negative constant current ΔI1 is only applied to the S-terminal 17, the determining unit 44 calculates ΔV1, and then determines whether ΔV1 is greater than or equal to a threshold. When the determining unit 44 determines that ΔV1 is greater than or equal to the threshold, the determining unit 44 determines that the disconnection failure of the P-terminal 16 occurs.

In the above embodiment, plural functions of a single component may be achieved by plural components, and one function of one component may be achieved by plural components. Further, plural functions of plural components may be achieved by one component, and one function achieved by plural components may be achieved by one component. A part of the above configuration according to the above embodiment may be canceled in a case where the above matters are stilled solved.

The present disclosure can be applied to various configurations such as a system including the ECU, a program executed by a computer to function as the ECU, a non-transitional substantial storage media including a semiconductor memory storing the program, or a method of sensing an abnormality of a connection between the ECU and an air-fuel ratio sensor.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. An air-fuel ratio sensor control unit connected with an air-fuel ratio sensor including a first cell, a second cell, a common terminal that is a terminal shared by the first cell and the second cell, a first terminal that is a terminal of the first cell opposite to the common terminal, and a second terminal that is a terminal of the second cell opposite to the common terminal, the air-fuel ratio sensor control unit comprising:

a common connection terminal connected with the common terminal;

a first connection terminal connected with the first terminal;

a second connection terminal connected with the second terminal;

a voltage control circuit controlling a voltage of the first connection terminal such that a voltage of the common connection terminal becomes a predetermined voltage;

a resistor including an end connected with the common connection terminal, the resistor through which a current flowing through the common connection terminal flows;

a voltage sensing circuit sensing a two-end voltage that is a voltage between two ends of the resistor;

a current applying circuit applying a constant current to the second connection terminal; and a determining unit sensing a change quantity of the two-end voltage generated by the constant current applied by the current applying circuit to the second connection terminal by using the voltage sensing circuit, the determining unit determining whether a disconnection failure of the first connection terminal occurs based on a sensing result of the change quantity.

2. The air-fuel ratio sensor control unit according to claim 1, wherein
the first cell is an oxygen pump cell, and the second cell is an electromotive force cell.

3. The air-fuel ratio sensor control unit according to claim 2, wherein
the resistor is equivalent to a resistor that is used to sense a current flowing through the first cell as an output of the air-fuel ratio sensor.

4. The air-fuel ratio sensor control unit according to claim 3, wherein
the voltage sensing circuit is equivalent to a circuit that is used to sense the current flowing through the first cell as the output of the air-fuel ratio sensor.

5. The air-fuel ratio sensor control unit according to claim 1, wherein
the current applying circuit is equivalent to a circuit that is used to apply the constant current to the second connection terminal to sense an impedance of the second cell.

6. The air-fuel ratio sensor control unit according to claim 1, wherein
the current applying circuit can apply a first constant current and a second constant current that flow in directions opposite to each other to the second connection terminal,
the air-fuel ratio sensor control unit further comprising:
a current control unit controlling the current applying circuit to sequentially apply the first constant current and the second constant current to the second connection terminal, wherein
the determining unit senses the change quantity by using the two-end voltage sensed by the voltage sensing circuit of when the current applying circuit applies the first constant current to the second connection terminal and the two-end voltage sensed by the voltage sensing circuit of when the current applying circuit applies the second constant current to the second connection terminal.

* * * * *